United States Patent
Lee et al.

(10) Patent No.: US 9,550,995 B2
(45) Date of Patent: Jan. 24, 2017

(54) COMPOSITION COMPRISING INHIBITOR AGAINST PAPSS2 GENE OR PROTEIN ENCODED BY GENE FOR INDUCING SENESCENCE IN TUMOR CELLS AND METHOD FOR INDUCING SENESCENCE IN TUMOR CELLS USING THE SAME

(71) Applicants: Korea Institute of Radiological & Medical Sciences, Seoul (KR); Inha University Research and Business Foundation, Incheon (KR)

(72) Inventors: Jae-Seon Lee, Seoul (KR); Seung Hee Jung, Seoul (KR); Bong Cho Kim, Gyeonggi-do (JP); Hyung Chul Lee, Seoul (KR); Na-Kyung Han, Seoul (KR); Mi-Na Hong, Seoul (KR)

(73) Assignees: Korea Institute of Radiological & Medical Sciences, Seoul (KR); Inha University Research and Business Foundation, Incheon (KR)

( * ) Notice: Subject to any disclaimer, the term of this patent is extended or adjusted under 35 U.S.C. 154(b) by 0 days.

(21) Appl. No.: 14/421,619

(22) PCT Filed: May 20, 2013

(86) PCT No.: PCT/KR2013/004408
§ 371 (c)(1),
(2) Date: Feb. 13, 2015

(87) PCT Pub. No.: WO2014/189156
PCT Pub. Date: Nov. 27, 2014

(65) Prior Publication Data
US 2016/0060633 A1 Mar. 3, 2016

(51) Int. Cl.
*C12N 15/11* (2006.01)
*C12N 15/113* (2010.01)
*A61K 31/713* (2006.01)

(52) U.S. Cl.
CPC ......... *C12N 15/1137* (2013.01); *A61K 31/713* (2013.01); *C12N 2310/14* (2013.01); *C12Y 207/07004* (2013.01)

(58) Field of Classification Search
None
See application file for complete search history.

(56) References Cited

U.S. PATENT DOCUMENTS

| 8,809,297 B2 | 8/2014 | Lee et al. | 424/130.1 |
| 2009/0214518 A1 | 8/2009 | Buckanovich et al. | 424/130.1 |
| 2010/0304409 A1 | 12/2010 | Lee et al. | 435/7.92 |

FOREIGN PATENT DOCUMENTS

| KR | 10-2009-0070276 | 7/2009 |
| KR | 10-2011-0130627 | 12/2011 |
| WO | WO 2004/013309 | 2/2004 |

OTHER PUBLICATIONS

Figueira et al., Correlation between MMPs and their inhibitors in breast cancer tumor tissue specimens and in cell lines with different metastatic potential, 2009, BMC Cancer, vol. 9, pp. 1-11.*
Gruvberger et al., Estrogen receptor status in breast cancer is associated with remarkably distinct gene expression patterns, 2001, Cancer Research, vol. 61, pp. 5979-5984.*
Sermeus et al., Hypoxia-induced modulation of apoptosis and BCL-2 family proteins in different cancer cell types, 2012, PLoS One, vol. 7, issue 11, e47519, pp. 1-16.*
Hermans et al., Loss of small region around the PTEN locus is a major chromosome 10 alteration in prostate cancer xenografts and cell lines, 2004, Genes, Chromosomes & Cancer, vol. 39, pp. 171-184.*
Ibeawuchi et al., Exploring prostate cancer genome reveals simultaneous losses of PTEN, FAS and PAPSS2 in patients with PSA recurrence after radical prostatectomy, 2015, International Journal of Molecular Sciences, vol. 16, pp. 3856-3869.*
Bapat et al., Gene expression: Protein interaction systems network modeling identifies transformation-associated molecules and pathways in ovarian cancer, 2010, Cancer Research, vol. 70, pp. 4809-4819.*
Letter/Written Disclosure of the Information Disclosure Statement for the above-referenced application, mailed on May 5, 2015, 2 pages.
Bradford, M., "A rapid and sensitive method for the quantitation of microgram quantities of protein utilizing the principle of protein-dye binding," Anal. Biochem. 72:248-254 (1976).
Campisi, J., "Suppressing cancer: the importance of being senescent," Science 309:886-887 (2005).
Chang et al., "Molecular determinants of terminal growth arrest induced in tumor cells by a chemotherapeutic agent," Proc. Natl. Acad. Sci. USA 99:389-394 (2002).
Collado et al., "Senescence in premalignant tumours, " Nature 436:642 (2005).
Dimri et al., "A biomarker that identifies senescent human cells in culture and in aging skin in vivo," Proc. Natl. Acad. Sci. USA 92:9363-9367 (1995).
English abstract of Korean Patent Publication No. KR 10-2009-0070276 (App No. KR 10-2007-0138230), Korean Intellectual Property Office, 1 page.
English abstract of Korean Patent Publication No. KR 10-2011-0130627 (App No. KR 10-2010-0050045), Korean Intellectual Property Office, 1 page.
Hemann, M. and M. Narita, "Oncogenes and senescence: breaking down in the fast lane," Genes & Dev. 21:1-5 (2007).

(Continued)

*Primary Examiner* — Dana Shin
(74) *Attorney, Agent, or Firm* — Dentons US LLP; Stephanie Seidman

(57) ABSTRACT

Provided is a composition for inducing tumor cell senescence and a method for inducing tumor cell senescence using the same. The composition can inhibit a PAPSS2 gene in a tumor cell to thereby induce senescence of the tumor cell, and if the composition is used concurrently with irradiation of the tumor cell, the composition can improve the sensitivity of the tumor cell to radiation.

2 Claims, 7 Drawing Sheets

(56) References Cited

OTHER PUBLICATIONS

Machine English translation of Korean Patent Publication No. KR 10-2009-0070276 (App No. KR 10-2007-0138230), Korean Intellectual Property Office, 16 pages.
Machine English translation of Korean Patent Publication No. KR 10-2011-0130627 (App No. KR 10-2010-0050045), Korean Intellectual Property Office, 16 pages.
Mason et al., "Molecular signature of oncogenic ras-induced senescence," Oncogene 23:9238-9246 (2004).
Narita, M and S. Lowe, "Senescence comes of age," Nature Medicine 11:920-922 (2005).
NCBI Accession No. NM_001015880, "*Homo sapiens* 3'-phosphoadenosine 5'-phosphosulfate synthase 2 (PAPSS2), transcript variant 2, mRNA," Updated on Mar. 15, 2015 [online][retrieved on Apr. 27, 2015] Retrieved from:<URL:ncbi.nlm.nih.gov/nuccore/62912490/ [5 pages].
NCBI Accession No. NM_004670, "*Homo sapiens* 3'-phosphoadenosine 5'-phosphosulfate synthase 2 (PAPSS2), transcript variant 1, mRNA," Updated on Mar. 15, 2015 [online][retrieved on Apr. 27, 2015] Retrieved from:<URL:ncbi.nlm.nih.gov/nuccore/NM_001015880 [5 pages].
Rebbaa, A. "Targeting senescence pathways to reverse drug resistance in cancer," Cancer Lett. 219:1-13 (2005).
Roninson et al., "If not apoptosis, then what? Treatment-induced senescence and mitotic catastrophe in tumor cells," Drug Resist Updates 4:303-313 (2001).
Sagiv et al., "Gene Expression following exposure to Celecoxib in humans: Pathways of inflammation and carcinogenesis are activated in tumors but not normal tissues," Digestion 84:169-184 (2011).
Sinha et al., "Polymer support oligonucleotide synthesis XVIJI1.2: use of beta-cyanoethyl-N,N-dialkylamino-/N-morpholino phosphoramidite of deoxynucleosides for the synthesis of DNA fragments simplifying deprotection and isolation of the final product," Nucleic Acids Research 12:4539-4557 (1984).
Sugrue et al., "Wild-type p53 triggers a rapid senescence program in human tumor cells lacking functional p53," Proc. Natl. Acad. Sci. USA 94:9648-9653 (1997).
Xue et al., "Senescence and tumour clearance is triggered by p53 restoration in murine liver carcinomas," Nature 445:656-660 (2007).
International Search Report, issued Feb. 3, 2014, in connection with International Patent Application No. PCT/KR2013/004408 [English Translation], 2 pages.
Letter/Written Disclosure of the Supplemental Information Disclosure Statement for the above-refereced application, filed herewith Apr. 21, 2016, 2 pages.
International Preliminary Report on Patentability, issued Nov. 24, 2015 and Written Opinion, mailed Feb. 3, 2014, in connection with International Patent Application No. PCT/KR2013/004408 [English Translation], 5 pages.

\* cited by examiner

COMPOSITION COMPRISING INHIBITOR AGAINST PAPSS2 GENE OR PROTEIN ENCODED BY GENE FOR INDUCING SENESCENCE IN TUMOR CELLS AND METHOD FOR INDUCING SENESCENCE IN TUMOR CELLS USING THE SAME

INCORPORATION BY REFERENCE OF SEQUENCE LISTING PROVIDED ELECTRONICALLY

An electronic version of the Sequence Listing is filed herewith, the contents of which are incorporated by reference in their entirety. The electronic file was created on Feb. 6, 2015, is 22 kilobytes in size, and titled 433SEQUS1.txt.

BACKGROUND OF THE INVENTION

Field of the Invention

The present invention relates to a composition for inducing senescence in tumor cells comprising an inhibitor against a 3'-phosphoadenosine 5'-phosphosulfate synthase 2 (PAPSS2) gene or protein encoded by the gene and a method for inducing senescence in tumor cells using the same.

Description of Related Art

Premature senescence, also known as stress-induced premature senescence, in tumor cells means senescence caused in tumor cells by various stimuli. In contrast to normal cells that undergo senescence after a particular number of cell division, tumor cells divide indefinitely due to changes in characteristics of replicative senescence during tumorigenesis, and it has long been known that tumor cells may not undergo cellular senescence. In recent years, however, various stimuli have been known to rapidly induce senescence in tumor cells, which is called stress-induced premature senescence (Sugrue et al., Proc. Natl. Acad. Sci. USA, 94:9648-9653, 1997; Mason et al., Oncogene, 23; 9238-9246, 2004). It has been reported that stress sources capable of inducing senescence in tumor cells are genotoxic chemicals (e.g., etoposide, cyclophosphamide, etc.), radiation, and UV light (Hemann and Narita, Genes & Dev., 21:1-5, 2007; Chang et al., Proc. Natl. Acad. Sci. USA, 99:389-394, 2002).

Suppression of tumor cell proliferation by inducing senescence in tumor cells through stress-induced premature senescence has recently been suggested as an effective mechanism for cancer therapy (Roninson et al., Drug Resist Updates, 4:303-313, 2001; Campisi, Science, 309:886-887, 2005), and studies on the mechanism of cellular senescence contributed to an improvement in the efficiency of cancer therapy (Narita and Lowe, Nature Medicine, 11:920-922, 2005). Moreover, a histological analysis of cancer patients with inhibited malignant progression of tumor reported that senescence was effectively induced in tumor cells (Collado et al., Nature, 436:642, 2005). In addition, the tumor suppressor protein p53 was reported to be implicated in the removal of tumor tissues through cellular senescence, as proven in an animal test (Xue et al., Nature, 445:656-660, 2007). This indicates that cellular senescence can be effectively applied to cancer therapy. In practice, the activation of the senescence mechanism in tumor cells makes it possible to treat cancer with lower doses of anticancer agents or radiation than does the activation of cell death mechanisms, thus improving the side effects associated with conventional cancer therapy and overcoming the resistance to cancer therapy of cancer cells which acquire the resistance to the cell death (Rebbaa, Cancer Lett, 219:1-13, 2005).

Meanwhile, 3'-phosphoadenosine 5'-phosphosulfate synthase 2 (PAPSS2) is a gene with National Center for Biotechnology Information (NCBI) Access No. NM_004670 (SEQ ID NO: 1) or NM_001015880 (SEQ ID NO: 2) and has not been known to be associated with premature senescence in tumor cells in the prior art.

Technical Problem

Accordingly, the present inventors have found that the inhibition of PAPSS2 gene expression in tumor cells induces senescence in tumor cells and the inhibition of PAPSS2 gene expression combined with radiation treatment in tumor cells enhances the sensitivity of tumor cells to radiation and completed the present invention.

Therefore, an object of the present invention is to provide a composition for inducing senescence in tumor cells. Moreover, another object of the present invention is to provide a method for inducing senescence in tumor cells using the composition for inducing senescence in tumor cells.

BRIEF SUMMARY OF THE INVENTION

To achieve the above objects, the present invention provides a composition for inducing senescence in tumor cells comprising an inhibitor against a 3'-phosphoadenosine 5'-phosphosulfate synthase 2 (PAPSS2) gene or protein encoded by the gene.

In the present invention, the gene may be a messenger ribonucleic acid (mRNA), and the inhibitor may be a small interfering RNA (siRNA) that can inhibit the mRNA.

In the present invention, the PAPSS2 gene comprises a nucleotide sequence of SEQ ID NO: 1 (NCBI Access No. NM_004670) or a nucleotide sequence of SEQ ID NO: 2 (NCBI Access No. NM_001015880). Moreover, the PAPSS2 gene comprises the nucleotide sequence of SEQ ID NO: 1 or the nucleotide sequence of SEQ ID NO: 2 in which one or more nucleotides are substituted, deleted, or inserted.

In the present invention, the protein encoded by the PAPSS2 gene comprises a polypeptide of SEQ ID NO: 3 or a polypeptide of SEQ ID NO: 4. Moreover, the protein encoded by the PAPSS2 gene comprises a polypeptide of SEQ ID NO: 3 or the polypeptide of SEQ ID NO: 4 in which one or more amino acids are substituted, deleted, or inserted.

In the present invention, it is obvious to those skilled in the art that the sequences of the PAPSS2 gene are merely examples, and the present invention is not limited thereto. Sequences having substantial sequence identity or substantial sequence homology to the sequences also fall within the scope of the present invention. As used herein, the term "substantial sequence identify" or "substantial sequence homology" is used to indicate that a sequence exhibits substantial, structural, or functional equivalence with another sequence. These differences are due to inherent variations in codon usage among different species, for example. Structural differences are considered de minimis if there is a significant amount of sequence overlap or similarity between two or more different sequences, even if the sequences differ in length or structure.

In the present invention, the inhibitor may be an siRNA that can inhibit the expression of the PAPSS2 gene. That is, the inhibitor may be a siRNA that can inhibit the expression of an mRNA for a 3'-phosphoadenosine 5'-phosphosulfate synthase 2 (PAPSS2) gene. The siRNA may be a double stranded siRNA composed of the sense sequence of SEQ ID NO: 5 (5'-ACA ACC UGU ACU CUU CCA A-3') and the antisense sequence SEQ ID NO: 6 (5'-UUG GAA GAG UAC AGG UUG U-3') complementary thereto. The siRNA may have two thymine residues (dTdT) attached at the 3' end of the sense sequence and/or the antisense sequence.

In the present invention, the inhibitor against the protein may be an antibody. The antibody may be a monoclonal antibody, a polyclonal antibody, and/or a recombinant antibody, which specifically binds to a protein encoded by a 3'-phosphoadenosine 5'-phosphosulfate synthase 2 (PAPSS2) gene, and may be a commercially available product or may be directly prepared using a well-known method.

In the present invention, the tumor cells may be cancer cells. The cancer may be at least one selected from the group consisting of liver cancer, stomach cancer, breast cancer, colon cancer, bone cancer, pancreatic cancer, head or neck cancer, uterine cancer, colorectal cancer, lung cancer, ovarian cancer, rectal cancer, esophageal cancer, small bowel cancer, anal cancer, fallopian tube carcinoma, endometrial carcinoma, cervical carcinoma, vaginal carcinoma, vulvar carcinoma, Hodgkin's disease, prostate cancer, bladder cancer, kidney cancer, ureter cancer, renal cell carcinoma, renal pelvis carcinoma, osteosarcoma, and central nervous system tumor. The cells may preferably be breast cancer cells or lung cancer cells, but not limited thereto.

The composition for inducing senescence in tumor cells of the present invention may be a pharmaceutical composition and can exhibit anticancer activity due to senescence induced in tumor cells by the inhibitor against the PAPSS2 gene or protein encoded by the gene contained in the composition for inducing senescence in tumor cells of the present invention.

The composition for inducing senescence in tumor cells of the present invention may comprise one or more carriers, diluents, excipients, or combinations thereof, which are commonly used in biological preparations. The pharmaceutically acceptable carrier is not particularly limited as long as it is suitable for in vivo delivery of the composition and may include one or more compounds described in Merck Index, 13th ed., Merck & Co. Inc., saline, sterile water, Ringer's solution, buffered saline, dextrose solution, maltodextrin solution, glycerol, ethanol and combinations thereof. If necessary, other general additives, such as antioxidant, buffer solution, anti-bacterial agent, etc., may be added to the composition. Moreover, the composition of the present invention may be formulated into injections such as aqueous solution, suspension, emulsion, etc., pills, capsules, granules, or tablets by further adding diluent, dispersant, surfactant, binder, and lubricant. Furthermore, the composition of the present invention may be formulated by suitable methods known in the art depending on the disease and/or ingredients.

The composition for inducing senescence in tumor cells of the present invention may be administered once a day at a dose of 0.01 ng/kg-100 mg/kg for adults with respect to a gene inhibitor, for example, a siRNA, to induce senescence in tumor cells, may be administered once a day at a dose of 2-10 mg/kg for adults with respect to a gene inhibitor, for example, an antibody, and may be administered in the usual manner via intravenous, intraarterial, intraperitoneal, intramuscular, intraperitoneal, intrasternal, percutaneous, intranasal, inhalation, topical, rectal, oral, intraocular or intradermal routes.

A therapeutically effective amount of the composition for inducing senescence in tumor cells of the present invention may vary depending on various factors such as administration route, target site, a patient's condition, etc. Therefore, the dose to be used in human should be determined as an appropriate amount in terms of both safety and effectiveness. It is possible to extrapolate the dose to be used in human from an effective amount determined in animal tests.

To achieve the above objects, the present invention provides a method for inducing senescence in tumor cells, wherein the method comprising treating tumor cells with a composition for inducing senescence in tumor cells comprising an inhibitor against a 3'-phosphoadenosine 5'-phosphosulfate synthase 2 (PAPSS2) gene or protein encoded by the gene.

In the present invention, the cells may be tumor cells of a mammal other than a human. The tumor cells may preferably be cancer cells. The cancer may be at least one selected from the group consisting of liver cancer, stomach cancer, breast cancer, colon cancer, bone cancer, pancreatic cancer, head or neck cancer, uterine cancer, colorectal cancer, lung cancer, ovarian cancer, rectal cancer, esophageal cancer, small bowel cancer, anal cancer, fallopian tube carcinoma, endometrial carcinoma, cervical carcinoma, vaginal carcinoma, vulvar carcinoma, Hodgkin's disease, prostate cancer, bladder cancer, kidney cancer, ureter cancer, renal cell carcinoma, renal pelvis carcinoma, osteosarcoma, and central nervous system tumor. The cells may preferably be breast cancer cells or lung cancer cells, but not limited thereto.

In the present invention, the method for inducing senescence in tumor cells may further comprises treating the cells with radiation.

In the present invention, the radiation may be gamma rays, and the gamma rays may be irradiated at a dose of 2 to 6 Gy, but not limited thereto.

In the method of the present invention, the treatment of the tumor cells with a composition for inducing senescence in tumor cells comprising an inhibitor against a PAPSS2 gene or protein encoded by the gene may be performed simultaneously or sequentially with the treatment of the tumor cells with radiation.

To achieve the above objects, the present invention provides a use of an inhibitor against a PAPSS2 gene or protein encoded by the gene for the preparation of a composition for inducing senescence in tumor cells.

To achieve the above objects, the present invention provides a use of an inhibitor against a PAPSS2 gene or protein encoded by the gene for the preparation of a composition for inducing senescence in tumor cells, which enhances the sensitivity of tumor cells to radiation.

Advantageous Effects

The composition for inducing senescence in tumor cells according to the present invention can induce senescence in tumor cells by inhibiting PAPSS2 gene expression in tumor cells and enhance the sensitivity of tumor cells to radiation when used in combination with the treatment of tumor cells with radiation.

DETAILED DESCRIPTION OF THE INVENTION

Hereinafter, the present invention will be described in more detail with reference to the following Examples. However, it should be understood that the following Examples are not intended to limit the scope of the present invention, but are intended to facilitate understanding the present invention.

Example 1

Identification of Genes with Expression Increased by Radiation-Induced Senescence in Tumor Cells 1-1 Cell Culture Human breast cancer cell line MCF-7 (ATCC, USA) was cultured in Dulbeco's Modified Eagle's Medium (DMEM) containing 10% fatal bovine serum (FBS; Welgene, Korea), 100 μg/ml streptomycin, and 100 units/ml penicillin (Gibco BRL) in an incubator maintained at 5% CO2 and 37° C.

Human lung cancer cell line H460 (ATCC, USA) was cultured in Dulbeco's Modified Eagle's Medium (DMEM) containing 10% fatal bovine serum (FBS; Welgene, Korea), 100 μg/ml streptomycin, and 100 units/ml penicillin (Gibco BRL) in an incubator maintained at 5% $CO_2$ and 37° C.

The human breast cancer cell line MCF-7 was exposed to 6 Gy gamma-rays from $^{137}Cs$ gamma-ray source (Atomic Energy of Canada Ltd., Mississauga, Ontario, Canada) at a dose rate of 3.81 Gy/min and then cultured in an incubator with 5% $CO_2$ at 37° C. for 1 to 4 days.

The human lung cancer cell line H460 was exposed to 6 Gy gamma-rays from $^{137}Cs$ gamma-ray source (Atomic Energy of Canada Ltd., Mississauga, Ontario, Canada) at a dose rate of 3.81 Gy/min and then cultured in an incubator with 5% $CO_2$ at 37° C. for 1 to 4 days.

Moreover, cells of the human breast cancer cell line MCF-7, which were not exposed to gamma-irradiation, were used as a control. Also, cells of the human lung cancer cell line H460, which were not exposed to gamma-irradiation, were used as a control.

1-2 Identification of Radiation-Induced Senescence

Figure 1:
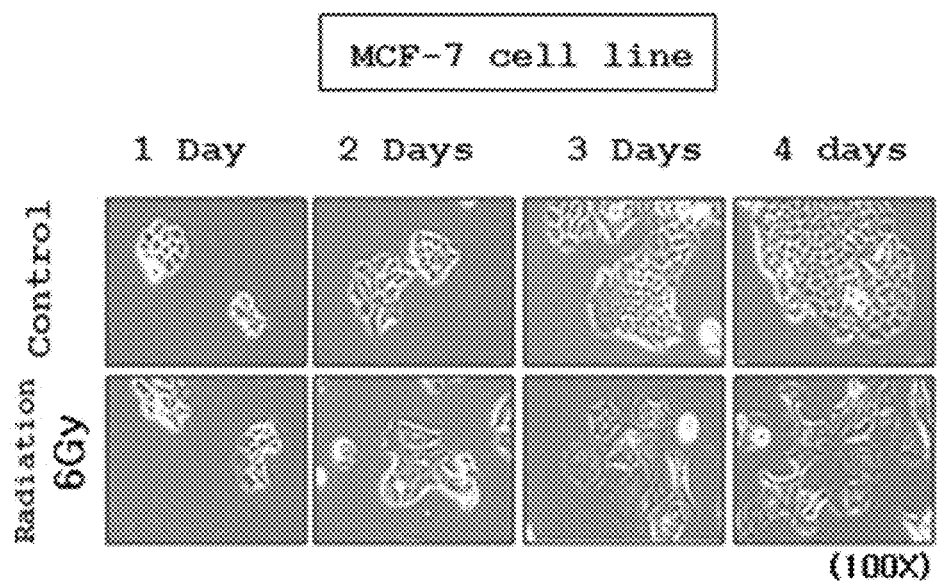
FIG. 1 shows the results of microscopic observation for each day in the control group and the irradiation group of human breast cancer cell line MCF-7.

To identify the induction of cellular senescence, characteristic changes in cell morphology of the control group of Example 1-1 and the human breast cancer cell line MCF-7 at 4 days after irradiation were observed under a microscope (ECLIPSE TE300, Nikon), and the results are shown in FIG. 1 (observed under a microscope for each day indicated in FIG. 1). As a result, it can be seen that the human breast cancer cell line MCF-7 at 4 days after irradiation became large in size and flat, which are characteristics of senescent cells, unlike the control group.

Figure 2:
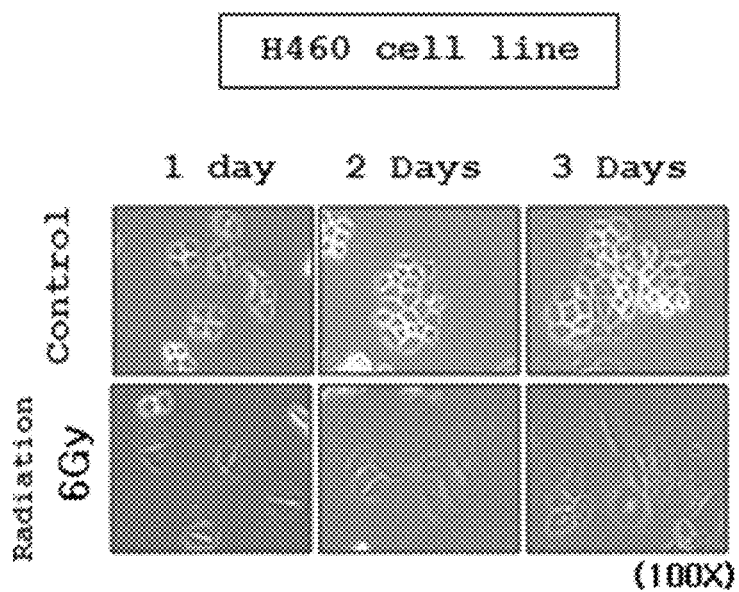
FIG. 2 shows the results of microscopic observation for each day in the control group and the irradiation group of human lung cancer cell line H460.

Moreover, to identify the induction of cellular senescence, characteristic changes in cell morphology of the control group of Example 1-1 and the human lung cancer cell line H460 at 3 days after irradiation were observed under a microscope (ECLIPSE TE300, Nikon), and the results are shown in FIG. 2 (observed under a microscope for each day indicated in FIG. 2). As a result, it can be seen that the human lung cancer cell line H460 at 3 days after irradiation H450 became large in size and flat, which are characteristics of senescent cells, unlike the control group.

1-3 Identification of Genes with Expression Changed by Radiation-Induced Senescence Using Microarray Analysis The human breast cancer cell line MCF-7 at 4 days after irradiation, prepared in Example 1-1, was washed with phosphate buffered saline (PBS) and subjected to RNA isolation using TRI Reagent (MRC, Inc. Cat #TR-118). The total RNA thus isolated was quantified using a UV spectrophotometer (Ultrospec 3100 PRO, Amersham Bioscience). cDNA was synthesized from 500 ng of the total RNA using reverse transcriptase, followed by in vitro amplification/transcription (Illumina TotalPrep RNA Amplification kit, Ambion Inc.) to synthesize biotinylated cRNA. 1.5 μg of the amplified biotinylated cRNA was hybridized to the BeadChip (Illumina Human-6 BeadChip Illumina, Inc.) and visualized with Cy3 fluorescence dye (Amersham Fluorolink streptavidin-Cy3, GE Healthcare Bio-Sciences). The chip was scanned on a confocal scanner (BeadStation 500GXDW; Illumina, Inc.) to detect hybridized signals which were then analyzed using Illumina BeadStudio software.

The microarray analysis performed in the above manner identified genes whose mRNA levels were changed in the radiation-induced senescent cells as follows (see Table 1).

Moreover, the identification of genes with expression changed by radiation-induced senescence using microarray analysis was also performed on the human lung cancer cell line H460, instead of the breast cancer cell line MCF-7, in the same manner as in Example 1-3, and the results are shown together in the following Table 1.

TABLE 1

Gene with expression of mRNA changed by radiation-induced senescence in tumor cells

| | Rate of increase in expression[1] | | | | |
|---|---|---|---|---|---|
| | MCF-7 | | | | H460 |
| Gene | 1 day[2] | 2 days | 3 days | 4 days | 4 days |
| PAPSS2 | 1.1 | 1.4 | 1.8 | 3 | 2.2 |

[1]Rate compared to the control without irradiation
[2]days after irradiation (6 Gy)

As shown in Table 1, it can be seen that the expression of the PAPSS2 gene increased in the senescence-induced human breast cancer cell line MCF-7 or human lung cancer cell line H460 after irradiation, compared to the control group.

1-4 Identification of Genes with Expression Changed by Radiation-Induced Senescence Using Western Blotting Analysis The human breast cancer cell line MCF-7 at 1 to 4 days after irradiation, prepared in the same manner as in Example 1-1, was washed with PBS and lysed with a cell lysis buffer (50 mM Tri-HCl, 1% NP-40, 0.25% sodium deoxycholate, 150 mM NaCl, 1 mM PMSF, 50 mM NaF, 0.2 mM $Na_3VO_4$, 10 μg/ml aprotinin, 2 μg/ml leupeptin) to extract proteins, and the extracted proteins were centrifuged at 11,000 rpm for 10 minutes. Then, the supernatant was collected, and the proteins were quantified using the Bradford method (Bradford, M., Anal. Biochem. 72:248-254 (1976)). 20 μg of protein was added to 2×SDS loading buffer (60 mM Tris-Cl (pH 6.8), 25% glycerol, 2% SDS, 14.4 mM mercaptoethanol, 0.1% bromophenol blue), and the mixture was heated at 95° C. for 5 minutes, followed by electrophoresis at 80 V for 2 hours on a 8% to 10% SDS polyacrylamide gel.

The proteins separated by electrophoresis were transferred onto a nitrocellulose membrane (Whatman), which was then blocked in PBS containing 5% skim milk for 1 hour at room temperature, and then primary antibodies diluted to 1:500 to 1:1000 were added to the membrane and reacted at 4° C. for 16 hours. The primary antibodies used were a polyclonal anti-PAPSS2 antibody (polyclonal anti-PAPSS2 Ab, Santa Cruz), a polyclonal anti-p21 antibody (polyclonal anti-p21 Ab, Santa Cruz), a polyclonal anti-actin antibody (polyclonal anti-actin Ab, Santa Cruz), a polyclonal anti-p53 antibody (polyclonal anti-p53 Ab, Leica), and an anti-phospho-pRb (p-pRb) antibody specifically recognizing only the Ser 807/811 phosphorylated form of pRb (anti-phospho-pRb Ab, Cell Signaling), and a horseradish peroxidase-conjugated anti-rabbit or anti-mouse antibody (HRP conjugated goat anti-rabbit IgG, HRP conjugated goat anti-mouse IgG, Santa Cruz) was used as a secondary antibody to detect the protein expression with enhanced chemiluminescence (ECL) reagent (Amersham). The results of the expression of PAPSS2 protein are shown in FIG. 3.

Moreover, the human lung cancer cell line H460 at 1 to 3 days after irradiation, prepared in the same manner as in Example 1-1, was washed with PBS and lysed with a cell lysis buffer (50 mM Tri-HCl, 1% NP-40, 0.25% sodium deoxycholate, 150 mM NaCl, 1 mM PMSF, 50 mM NaF, 0.2 mM $Na_3VO_4$, 10 g/ml aprotinin, 2 g/ml leupeptin) to extract proteins, and the extracted proteins were centrifuged at 11,000 rpm for 10 minutes. Then, the supernatant was collected, and the proteins were quantified using the Bradford method (Bradford, M., Anal. Biochem. 72:248-254 (1976)). 20 μg of protein was added to 2×SDS loading buffer (60 mm Tris-Cl (pH 6.8), 25% glycerol, 2% SDS, 14.4 mM mercaptoethanol, 0.1% bromophenol blue), and the mixture was heated at 95° C. for 5 minutes, followed by electrophoresis at 80 V for 2 hours on a 8% to 10% SDS polyacrylamide gel.

The proteins separated by electrophoresis were transferred onto a nitrocellulose membrane (Whatman), which was then blocked in PBS containing 5% skim milk for 1 hour at room temperature, and then primary antibodies diluted to 1:500 to 1:1000 were added to the membrane and reacted at 4° C. for 16 hours. The primary antibodies used were a polyclonal anti-PAPSS2 antibody (polyclonal anti-PAPSS2 Ab, Santa Cruz), a polyclonal anti-p21 antibody (polyclonal anti-p21 Ab, Santa Cruz), a polyclonal anti-actin antibody (polyclonal anti-actin Ab, Santa Cruz), a polyclonal anti-p53 antibody (polyclonal anti-p53 Ab, Leica), and an anti-phospho-pRb (p-pRb) antibody specifically recognizing only the Ser 807/811 phosphorylated form of pRb (anti-phospho-pRb Ab, Cell Signaling), and a horseradish peroxidase-conjugated anti-rabbit or anti-mouse antibody (HRP conjugated goat anti-rabbit IgG, HRP conjugated goat anti-mouse IgG, Santa Cruz) was used as a secondary antibody to detect the protein expression with enhanced chemiluminescence (ECL) reagent (Amersham). The results of the expression of PAPSS2 protein are shown in FIG. 4.

Figure 3:
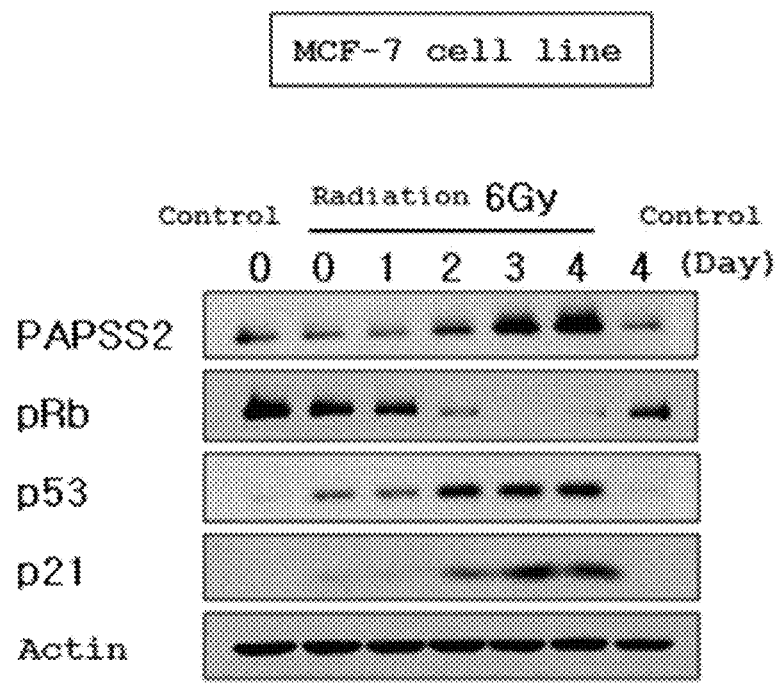
FIG. 3 shows the results of Western blotting illustrating the increased expression of PAPSS2, p53, and p21 and the decreased phosphorylation Rb for each day up to 4 days after irradiation in human breast cancer cell line MCF-7.
Figure 4:
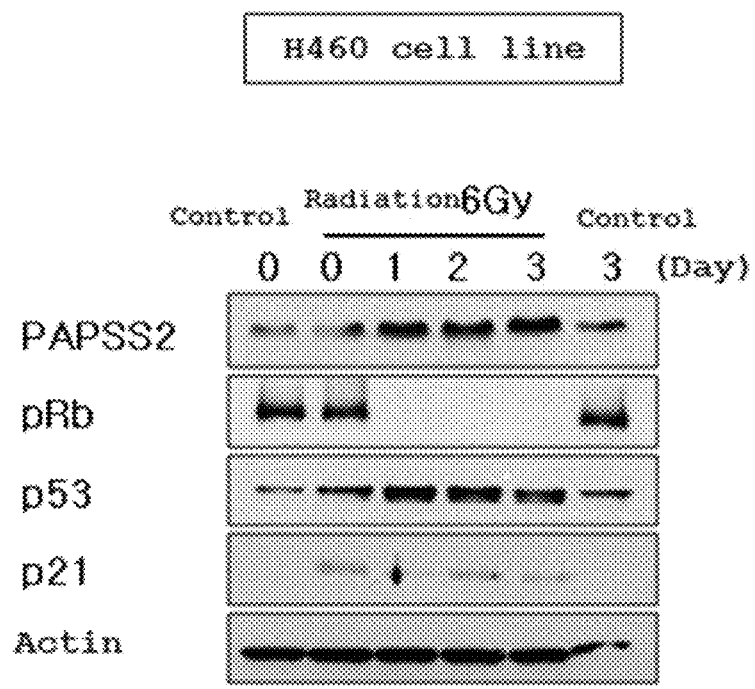
FIG. 4 shows the results of Western blotting illustrating the increased expression of PAPSS2, p53, and p21 and the decreased phosphorylation of Rb for each day up to 3 days after irradiation in human lung cancer cell line H460.

In FIGS. 3 and 4, actin, a housekeeping gene which is expressed at constant levels in all cells, was used as a reference to determine whether the same amount of proteins was analyzed.

The results of the Western blotting analysis confirm that the phosphorylation of senescence-specific Rb decreases and the expression of p53 and p21 increases by irradiation in the human breast cancer cell line MCF-7 or the human lung cancer cell line H460 after irradiation, indicating the induction of senescence by radiation. Moreover, the results of the Western blotting analysis confirm that the expression of PAPSS2 gene increases in the senescence-induced human breast cancer cell line MCF-7 or human lung cancer cell line H460 after irradiation, i.e., the expression level of PAPSS2 protein increases compared to the control group.

Example 2

Identification of Induction of Senescence in Tumor Cells by PAPSS2 Gene Inhibitor (siRNA)

2-1 Treatment with Small Interfering RNA (siRNA) Against PAPSS2 Gene

To examine the effect of a reduction in the expression level of PAPSS2 gene, the human breast cancer cell line MCF-7 (ATCC, USA) was cultured in DMEM containing 10% fatal bovine serum (FBS; Welgene, Korea) and an antibiotic (Gibco BRL) and passed to 60-mm culture dishes one day before treatment with siRNA. Then, 2 μl of RNAiMAX (Invitrogen, Cat #13778-075) and OptiMEM® I medium (Invitrogen, Cat #31985) were added to the cells, which were then treated with a small interfering RNA against PAPSS2 gene (siPAPSS2; a double stranded siRNA composed of the nucleotide sequence of 5'-ACA ACC UGU ACU CUU CCA A-3' (SEQ ID NO: 5) and the nucleotide sequence of 5'-UUG GAA GAG UAC AGG UUG U-3' (SEQ ID NO: 6), in which two thymine residues (dTdT) are attached at the 3' end of each sequence) at a concentration of 50 nM, followed by incubation for 6 hours. After the medium was replaced by DMEM containing 10% FBS (Welgene), 100 μg/ml streptomycin, and 100 units/ml penicillin (Gibco BRL), the cells were incubated in an incubator with 5% $CO_2$ at 37° C. for 4 days.

Moreover, cells of the human breast cancer cell line MCF-7 treated with non-specific small interfering RNA (siControl; a double stranded siRNA composed of the nucleotide sequence of 5'-CCU ACG CCA CCA AUU UCG U-3' (SEQ ID NO: 7) and the nucleotide sequence of 5'-ACG AAA UUG GUG GCG UAG G-3' (SEQ ID NO: 8), in which two thymine residues (dTdT) are attached at the 3' end of each sequence) were used as a control.

All siRNAs were synthesized in Bioneer (Korea). In detail, β-cyanoethyl phosphoramidite was used for the synthesis of siRNAs by linking phosphodiester bonds that form the backbone of DNA (see Sinha et al., Nucleic Acids Research, 12:4539-4557, 1984). That is, using an RNA synthesizer (Perceptive Biosystems 8909, PE Biosystems, USA), a series of processes including deblocking, coupling, oxidation and capping were repeated on a solid support, to which nucleotides were attached, to obtain a reactant containing RNAs of a desired length. Then, RNA was isolated from the reactant using HPLC LC918 (Japan Analytical Industry, Japan) equipped with Daisogel C18 (Daiso, Japan) and its sequence was analyzed by MALDI-TOF mass spectroscopy (Shimadzu, Japan). Then, sense and antisense RNA strands were combined to prepare the desired double stranded siRNA.

Figure 5:
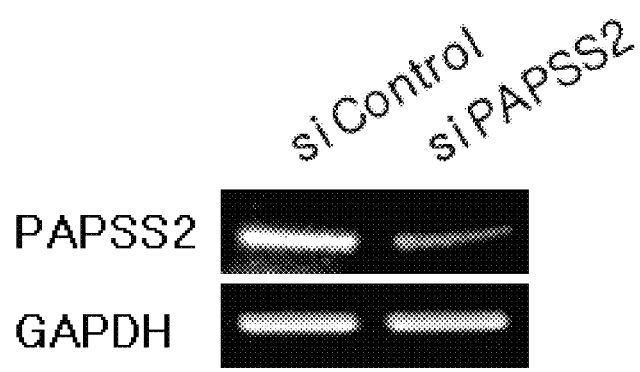
FIG. 5 shows the results of reverse transcriptase-PCR illustrating the change in the expression level of mRNA in the control group (treated with siControl) and the experimental group (treated with siPAPSS2) in human breast cancer cell line MCF-7.

2-2 Determination of Decrease in Protein Expression by Specific Small Interfering RNA FIG. 5 shows the results of reverse transcriptase-PCR illustrating the reduction in the expression of PAPSS2 mRNA in the human breast cancer cell line MCF-7 after treatment with specific small interfering RNA (siPAPSS2) or non-specific small interfering RNA (siControl) against PAPSS2. In detail, the human breast cancer cell line MCF-7 was treated with the specific small interfering RNA (siPAPSS2) or non-specific small interfering RNA (siControl) against PAPSS2, and after 2 days, the cell medium was discarded, the cells were washed twice with PBS. Then, RNA was extracted from the cells with 1 ml Trizol (Molecular research center, MRC), and cDNA was synthesized using a thymine residue (oligo dT), which selectively recognizes an adenosine residue at the 3' end of RNA, and a reverse transcriptase (Invitrogen). The synthesized cDNA was used for the polymerase chain reaction (PCR) amplification of PAPSS2 gene using a forward primer (5'-GTCTCTCTGGT-GCTGGAAAA-3', SEQ ID NO: 9), and a reverse primer (5'-TGCGAATGGAGAAATAAAGC-3', SEQ ID NO: 10), followed by electrophoresis at 100 V for 30 minutes on a 1% agarose gel. The agarose gel was stained with ethidium bromide (EtBr, sigma) and observed under an ultraviolet lamp (Bio-Rad). In FIG. 5, GAPDH is a gene which is expressed at constant levels in all samples and indicates that the amounts of proteins used in all samples are the same.

As shown in FIG. 5, it can be seen that the expression of PAPSS2 mRNA in the breast cancer cell line MCF-7 significantly decreased in the experimental group (treated with siPAPSS2) compared to the control group (treated with siControl).

2-3 Identification of Cell Proliferation Rate Using Trypan Blue Staining

Figure 6:
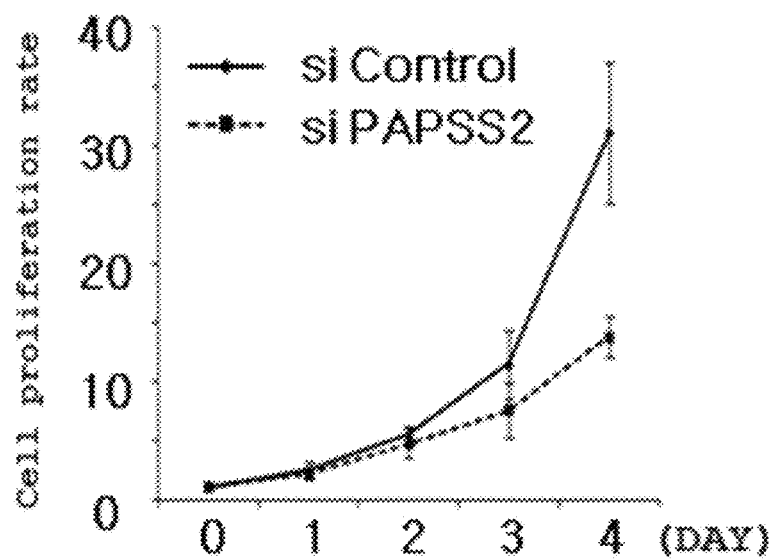
FIG. 6 shows the induction of senescence in human breast cancer cell line MCF-7 by a PAPSS2 gene inhibitor (siRNA) and is a graph illustrating the cell proliferation rate in the control group (treated with siControl) and the experimental group (treated with siPAPSS2).

FIG. 6 shows the cell proliferation rate obtained by treating the human breast cancer cell line MCF-7 with specific small interfering RNA (siPAPSS2) or non-specific small interfering RNA (siControl) against PAPSS2, culturing the cell line in an incubator with 5% $CO_2$ at 37° C. for 1 to 4 days, collecting cell supernatants on the days indicated in FIG. 6, splitting the cells using Trypsin, washing the cells twice with PBS, mixing the cells with 0.4% Trypan blue (NUNK) at a ratio of 1:1, leaving the cells at room temperature for 5 minutes, counting the number of cells, which were not stained with Trypan blue, on a hemocytometer (MARIENFELD) to calculate the cell proliferation rate as a percentage to the total number of cells.

FIG. 6 is a graph illustrating the cell proliferation rate in the control group (treated with siControl) and the experimental group (treated with siPAPSS2). In FIG. 6, the x-axis represents the days of cell culture after treatment with siPAPSS2 or siControl and the y-axis represents the cell proliferation rate based on the number of cells at 0 day. As shown in FIG. 6, it can be seen that the cell proliferation rate of the tumor cells (i.e., the human breast cancer cell line MCF-7) decreased in the experimental group treated with siPAPSS2 over time compared to the control group. Therefore, it can be seen from these results that the inhibition of the expression of PAPSS2 gene in tumor cells (e.g., the human breast cancer cell line MCF-7) induces senescence in tumor cells, which results in a decrease in cell proliferation rate.

2-4 Identification of Induction of Senescence in Tumor Cells by Colony Formation Assay The human breast cancer cell line MCF-7 treated with specific small interfering RNA (siPAPSS2) or non-specific small interfering RNA (siControl) against PAPSS2, prepared in the same manner as in Example 2-1, was distributed at a density of 500 cells in 60-mm dishes by passage. After incubation for 8 days, colonies thus formed were stained with a Diff Quick reagent (Sysmex Cat #38721). In detail, the medium was removed and the cells were washed once with PBS. Then, the cells were mixed softly with 0.5 mL of solution A and removed. And then the cells were mixed softly with 0.5 mL of solution B and removed. After that the cells were mixed softly with 0.5 mL of solution C and removed. Thereafter, the cells were rinsed with a sufficient amount of distilled water and dried at room temperature for 30 minutes, followed by colony counting (Image Product International #880).

Figure 7:
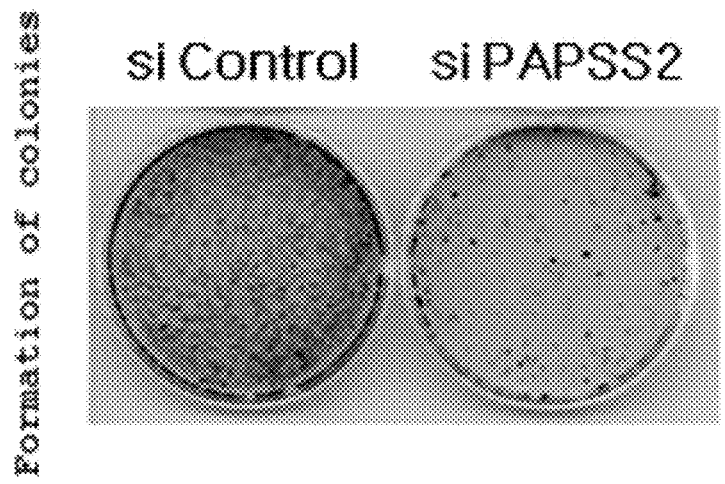
FIG. 7 shows the induction of senescence in human breast cancer cell line MCF-7 by a PAPSS2 gene inhibitor (siRNA) and is an image illustrating the formation of colonies of tumor cells over 8 days after treatment with specific small interfering RNA (siPAPSS2) or non-specific small interfering RNA (siControl) against PAPSS2, respectively.

FIG. 7 is an image illustrating the formation of colonies of tumor cells over 8 days after treatment with specific small interfering RNA (siPAPSS2) or non-specific small interfering RNA (siControl) against PAPSS2, respectively. As shown in FIG. 7, it can be seen that the formation of colonies of tumor cells significantly decreased in the tumor cell line treated with siPAPSS2 (the human breast cancer cell line MCF-7) compared to the control group. Therefore, it can be seen from these results that the inhibition of the expression of PAPSS2 gene in tumor cells (e.g., the human breast cancer cell line MCF-7) induces senescence in tumor cells, which results in a decrease in the formation of colonies of tumor cells.

2-5 Identification of Induction of Senescence in Tumor Cells by siPAPSS2 Using Senescence-Associated Beta-Galactosidase Activity Staining To identify the induction of senescence in tumor cells by radiation, senescence-associated beta-galactosidase activity staining was performed on the control group (treated with non-specific small interfering RNA in the human breast cancer cell line MCF-7) and the experimental group (treated with specific small interfering RNA in the human breast cancer cell line MCF-7) of Example 2-1. The control and experimental groups of Example 2-1 were treated with non-specific small interfering RNA (siControl) and specific small interfering RNA (siPAPSS2) against PAPSS2, respectively, followed by senescence-associated beta-galactosidase activity staining on the groups at 1 day, 2 days, 3 days, and 4 days, respectively. This staining was performed according to the Dimri method (Dimri et al., Proc. Natl. Acad. Sci. USA, 92:9363-9367, 1995) as follows.

Cells were washed twice with PBS and fixed at room temperature for 3 to 5 minutes in 3% formaldehyde. The fixed cells were washed once again with PBS and incubated with 5 mL of a β-galactosidase staining solution (1 mg/ml X-Gal, 40 mM citric acid/sodium phosphate (pH 6.0), 5 mM potassium ferrocyanide, 5 mM potassium ferricyanide, 150 mM sodium chloride, 2 mM magnesium chloride) in an incubator at 37° C. for 12 to 16 hours while the culture dishes were wrapped with foil so as to keep a dark condition.

Figure 8:
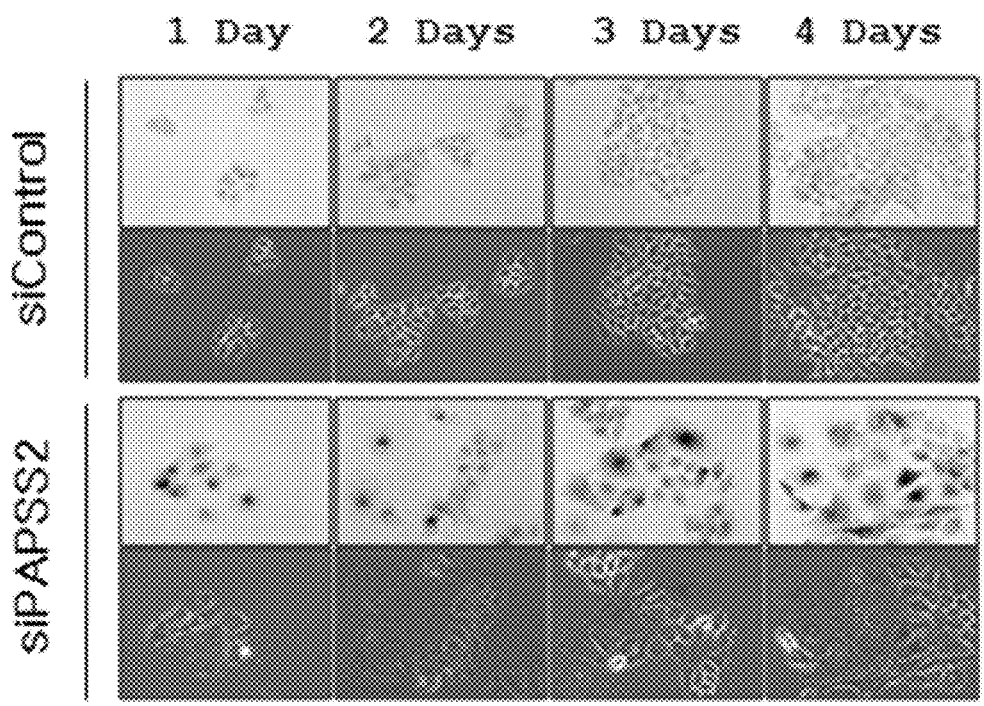
FIG. 8 shows images observed under a phase-contrast microscope after treatment of human breast cancer cell line MCF-7 with siControl and siPAPSS2, respectively, followed by staining with a reagent specific to activated senescence-associated beta-galactosidase on the days indicated in FIG. 8.
Figure 9:
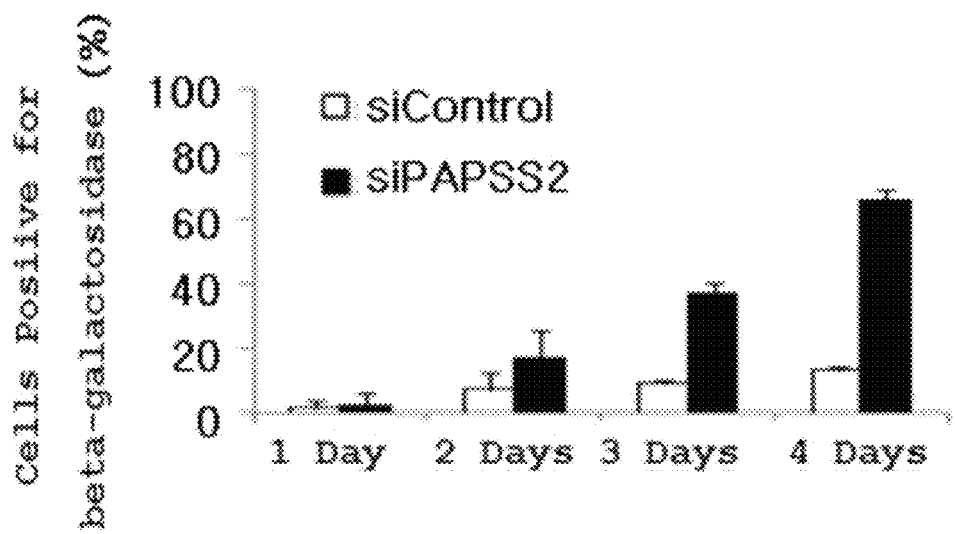
FIG. 9 is a graph illustrating the percentage of cells positive for senescence-associated beta-galactosidase after treatment of human breast cancer cell line MCF-7 with siControl and siPAPSS2, respectively, followed by staining with a reagent specific to activated senescence-associated beta-galactosidase on the days indicated in FIG. 9.

The beta-galactosidase activity level was measured under a phase-contrast microscope (ECLIPSE TE300, Nikon), and the results are shown in FIG. 8. Moreover, the number of stained cells after irradiation was measured using a microscope (ECLIPSE TE300, Nikon), and a graph representing the percentage of cells positive for senescence-associated beta-galactosidase is shown in FIG. 9.

It can be seen that the number of cells stained in the experimental group, i.e., the number of cells positive for senescence-associated beta-galactosidase increased, compared to the control group. In particular, it can be seen that the senescence occurred significantly in the experimental group treated with specific small interfering RNA (siPAPSS2) against PAPSS2 over time, compared to the control group.

Therefore, it can be seen from these results that the inhibition of the expression of PAPSS2 gene in tumor cells (e.g., the human breast cancer cell line MCF-7) induces senescence in tumor cells, thus exhibiting anticancer activity.

Example 3

Identification of Increase in Sensitivity of Tumor Cells to Radiation-Induced Senescence by Treatment with PAPSS2 Gene Inhibitor (siRNA)

3-1 Identification of Cell Proliferation Rate Using Trypan Blue Staining

The human breast cancer cell line MCF-7 was treated with specific small interfering RNA (siPAPSS2) or non-specific small interfering RNA (siControl) against PAPSS2, and the cell line was cultured in an incubator with 5% $CO_2$ at 37° C. for 24 hours, exposed to 2 Gy or 4 Gy gamma-rays from $^{137}Cs$ gamma-ray source (Atomic Energy of Canada Ltd., Mississauga, Ontario, Canada), and then cultured in an incubator for 3 days. The human breast cancer cell line MCF-7 was treated with non-specific small interfering RNA (siControl) against PAPSS2, and the cell line was cultured in an incubator with 5% $CO_2$ at 37° C. for 24 hours and then cultured in an incubator for 3 days, without being exposed to gamma-rays. The non-specific small interfering RNA (siControl) and the specific small interfering RNA (siPAPSS2) against PAPSS2 were prepared in the same manner as in Example 2-1 and used. After collecting all cell supernatants, the cells were split using Trypsin, washed twice with PBS, mixed with 0.4% Trypan blue (NUNK) at a ratio of 1:1, and left at room temperature for 5 minutes, and the number of cells, which were not stained with Trypan blue, was counted on a hemocytometer (MARIENFELD) to calculate the cell proliferation rate as a percentage to the total number of cells.

Figure 10:
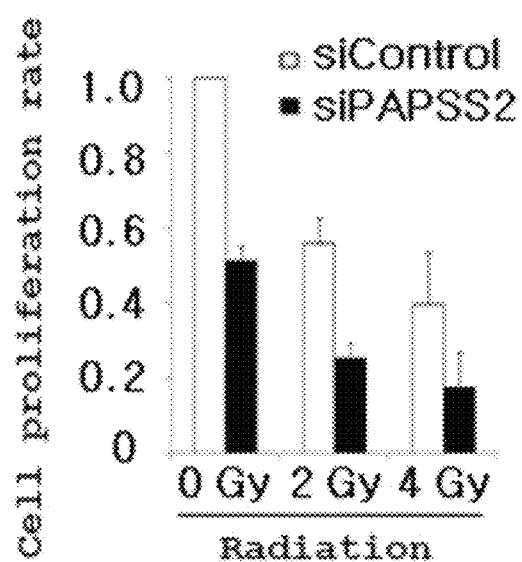
FIG. 10 is a graph illustrating the cell proliferation rate at 3 days after treatment of human breast cancer cell line MCF-7 with siControl and siPAPSS2, respectively, followed by gamma-irradiation at a dose of 2 or 4 Gy after 24 hours.

FIG. 10 is a graph illustrating the cell proliferation rate at 3 days after gamma-irradiation to the human breast cancer cell line MCF-7 at a dose of 2 or 4 Gy after 24 hours. In FIG. 10, the relative cell proliferation rate is shown with respect to the cell proliferation rate of 1 in the group in which the human breast cancer cell line MCF-7 was treated with non-specific small interfering RNA (siControl) without being exposed to gamma-rays.

As shown in FIG. 10, it can be seen that the cell proliferation rate of tumor cells (e.g., the human breast cancer cell line MCF-7) decreased over time in the group treated with siPAPSS2 compared to the control group. Therefore, it can be seen from these results that the inhibition of the expression of PAPSS2 gene in tumor cells (e.g., the human breast cancer cell line MCF-7) induces senescence in tumor cells, which results in a decrease in cell proliferation rate.

3-2 Identification of Induction of Senescence in Tumor Cells by Colony Formation Assay The human breast cancer cell line MCF-7 treated with specific small interfering RNA (siPAPSS2) or non-specific small interfering RNA (siControl) against PAPSS2 was distributed at a density of 500 cells in 60-mm dishes by passage. The non-specific small interfering RNA (siControl) and the specific small interfering RNA (siControl) against PAPSS2 were prepared in the same manner as in Example 2-1 and used. The cell line was cultured in an incubator with 5% $CO_2$ at 37° C. for 24 hours and exposed to 2 Gy or 4 Gy gamma-rays from $^{137}Cs$ gamma-ray source (Atomic Energy of Canada Ltd., Mississauga, Ontario, Canada), and then cultured in an incubator for 8 days. Then, the thus formed colonies were stained with a Diff Quick reagent (Sysmex Cat #38721). In detail, the medium was removed and the cells were washed once with PBS. Then, the cells were mixed softly with 0.5 mL of solution A and removed. And then the cells were mixed softly with 0.5 mL of solution B and removed. After that the cells were mixed softly with 0.5 mL of solution C and removed. Thereafter, the cells were rinsed with a sufficient amount of distilled water and dried at room temperature for 30 minutes, followed by analysis.

Figure 11:
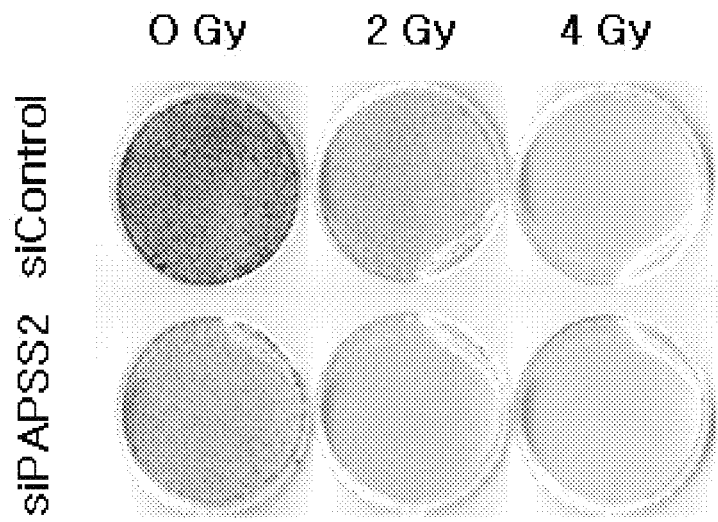
FIG. 11 is an image illustrating the formation of colonies of tumor cells over 8 days after treatment with specific small interfering RNA (siPAPSS2) or non-specific small interfering RNA (siControl) against PAPSS2, respectively, in combination with radiation treatment.

FIG. 11 is an image illustrating the formation of colonies of tumor cells over 8 days after treatment with specific small interfering RNA (siPAPSS2) or non-specific small interfering RNA (siControl) against PAPSS2, respectively, in combination with radiation treatment. As shown in FIG. 11, upon exposure to the same dose of radiation, the formation of colonies of tumor cells significantly decreased in the tumor cell line treated with siPAPSS2 (the human breast cancer cell line MCF-7) compared to the control group. Therefore, it can be seen that the sensitivity of tumor cells (e.g., the human breast cancer cell line MCF-7) to the induction of senescence by radiation increases in the group treated with the PAPSS2 gene inhibitor (siRNA), which results in a decrease in the formation of colonies of tumor cells, compared to the control group. That is, it can be seen from these results that the inhibition of the expression of PAPSS2 gene in tumor cells (e.g., the human breast cancer cell line MCF-7) increases the sensitivity of tumor cells to the induction of senescence by radiation, thus exhibiting greater anticancer activity.

3-3 Identification of Increase in Sensitivity of Tumor Cells to Radiation-Induced Senescence by siPAPSS2 Using Senescence-Associated Beta-Galactosidase Activity Staining The control and experimental groups were treated with non-specific small interfering RNA (siControl) and specific small interfering RNA (siPAPSS2) against PAPSS2, respectively, cultured in an incubator with 5% $CO_2$ at 37° C. for 24 hours, and exposed to 2 Gy or 4 Gy gamma-rays from $^{137}Cs$ gamma-ray source (Atomic Energy of Canada Ltd., Mississauga, Ontario, Canada), and then cultured in an incubator for 3 days, followed by senescence-associated beta-galactosidase activity staining. The non-specific small interfering RNA (siControl) and the specific small interfering RNA (siPAPSS2) against PAPSS2 were prepared in the same manner as in Example 2-1 and used. This staining was performed according to the Dimri method (Dimri et al., Proc. Natl. Acad. Sci. USA, 92:9363-9367, 1995) as follows.

Cells were washed twice with PBS and fixed at room temperature for 3 to 5 minutes in 3% formaldehyde. The fixed cells were washed once again with PBS and incubated with 5 mL of a β-galactosidase staining solution (1 mg/ml X-Gal, 40 mM citric acid/sodium phosphate (pH 6.0), 5 mM potassium ferrocyanide, 5 mM potassium ferricyanide, 150 mM sodium chloride, 2 mM magnesium chloride) in an incubator with 5% $CO_2$ at 37° C. for 12 to 16 hours while the culture dishes were wrapped with foil so as to keep a dark condition.

Figure 12:
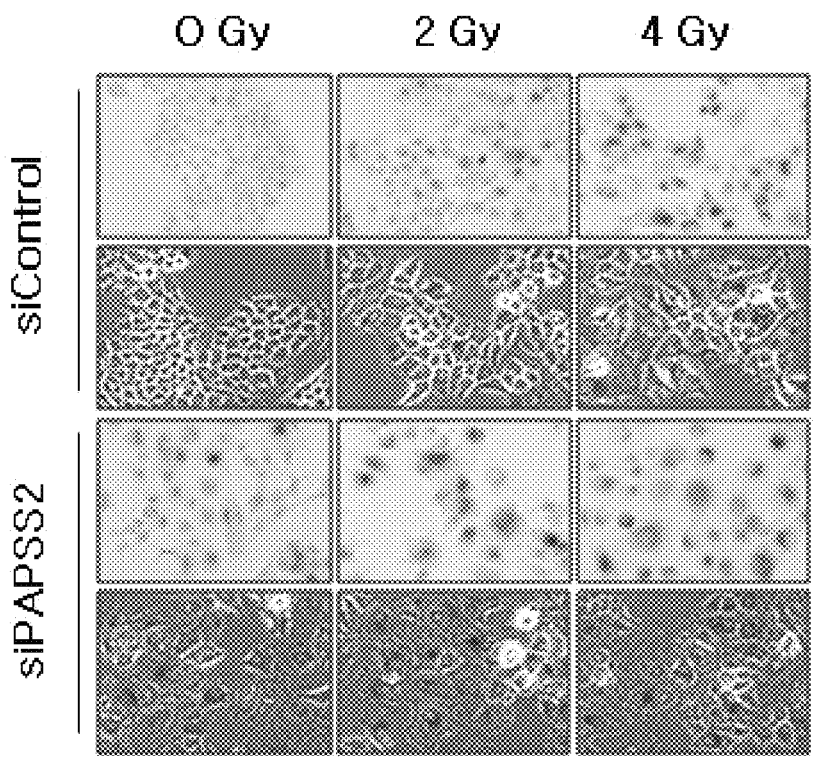
FIG. 12 shows images observed under a phase-contrast microscope after treatment of human breast cancer cell line MCF-7 with siControl and siPAPSS2, respectively, and gamma-irradiation at a dose of 0, 2 or 4 Gy, followed by staining with a reagent specific to activated senescence-associated beta-galactosidase after 3 days.
Figure 13:
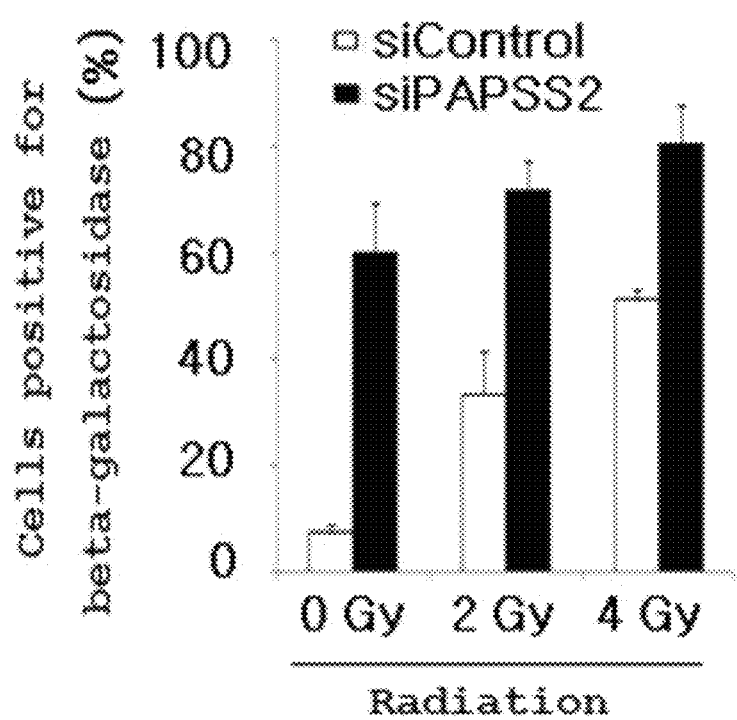
FIG. 13 is a graph illustrating the percentage of cells positive for senescence-associated beta-galactosidase after treatment of human breast cancer cell line MCF-7 with siControl and siPAPSS2, respectively, and gamma-irradiation at a dose of 0, 2 or 4 Gy, followed by staining with a reagent specific to activated senescence-associated beta-galactosidase after 3 days.

The beta-galactosidase activity level was measured under a phase-contrast microscope (ECLIPSE TE300, Nikon), and the results are shown in FIG. 12. Moreover, the number of stained cells was measured using a microscope (ECLIPSE TE300, Nikon) after irradiation, and a graph representing the percentage of cells positive for senescence-associated beta-galactosidase is shown in FIG. 13.

As shown in FIG. 12, upon exposure to the same dose of radiation, the percentage of cells that became large in size and flat, which are characteristics of senescent cells, increased in the group treated with the PAPSS2 gene inhibitor (siRNA) compared to the control group. Moreover, as shown in FIG. 13, upon exposure to the same dose of radiation, the percentage of cells positive for senescence-associated beta-galactosidase increased in the group treated with the PAPSS2 gene inhibitor (siRNA) compared to the control group. Therefore, it can be seen that the sensitivity of tumor cells (e.g., the human breast cancer cell line MCF-7) to the induction of senescence by radiation increases in the group treated with the PAPSS2 gene inhibitor (siRNA) compared to the control group. That is, it can be seen from these results that the inhibition of the expression of PAPSS2 gene in tumor cells (e.g., the human breast cancer cell line MCF-7) increases the sensitivity of tumor cells to the induction of senescence by radiation, thus exhibiting greater anticancer activity.

As described above, the composition for inducing senescence in tumor cells according to the present invention can induce senescence in tumor cells by inhibiting PAPSS2 gene expression in tumor cells and can be used to enhance the sensitivity of tumor cells to radiation when used in combination with the treatment of tumor cells with radiation.

The invention claimed is:

1. A method for inducing senescence in a MCF-7 breast cancer cell, the method comprising treating the MCF-7 breast cancer cell with a composition comprising an inhibitor of a 3'-phosphoadenosine 5'-phosphosulfate synthase 2 (PAPSS2) gene, wherein the inhibitor is siRNA that has the sense sequence set forth as SEQ ID NO: 5, and the antisense sequence set forth as SEQ ID NO: 6.

2. The method of claim 1, further comprising treating the MCF-7 breast cancer cell with radiation.

* * * * *

SEQUENCE LISTING

```
<160> NUMBER OF SEQ ID NOS: 10

<210> SEQ ID NO 1
<211> LENGTH: 3859
<212> TYPE: DNA
<213> ORGANISM: Homo sapiens
<220> FEATURE:
<221> NAME/KEY: mRNA
<222> LOCATION: (1)...(3859)
<223> OTHER INFORMATION: Homo sapiens 3'-phosphoadenosine
      5'-phosphosulfate synthase 2 (PAPSS2), transcript variant 1, mRNA,
      Access No. NM_004670

<400> SEQUENCE: 1
ctaggcggcg gcggccgggt ccccaaggct gggcgctgct tgcggaaccg acggggcgga      60
gaggagcgtg gcgggaggag gagtaggaga aggggggctgg tcaagggaag tgcgacgtgt     120
ctgcggagcc ttttatacc tccttcccgg gagtccggca gccgctgctg ctgctgctgc      180
tgctgctgcc gccgccgccg ccgccgtccc tgcgtccttc ggtctctgct cccgggaccc     240
gggctccgcc gcagccagcc agcatgtcgg ggatcaagaa gcaaaagacg gagaaccagc     300
agaaatccac caatgtagtc tatcaggccc accatgtgag caggaataag agagggcaag     360
tggttggaac aaggggtggg ttccgaggat gtaccgtgtg gctaacaggt ctctctggtg     420
ctggaaaaac aacgataagt tttgccctgg aggagtacct tgtctcccat gccatccctt     480
gttactccct ggatggggac aatgtccgtc atggccttaa cagaaatctc ggattctctc     540
ctggggacag agaggaaaat atccgccgga ttgctgaggt ggctaagctg tttgctgatg     600
ctggtctggt ctgcattacc agctttattt ctccattcgc aaaggatcgt gagaatgccc     660
```

```
gcaaaataca tgaatcagca gggctgccat tctttgaaat atttgtagat gcacctctaa    720
atatttgtga aagcagagac gtaaaaggcc tctataaaag ggccagagct ggggagatta    780
aaggatttac aggtattgat tctgattatg agaaacctga aactcctgag cgtgtgctta    840
aaaccaattt gtccacagtg agtgactgtg tccaccaggt agtggaactt ctgcaagagc    900
agaacattgt accctatact ataatcaaag atatccacga actctttgtg ccggaaaaca    960
aacttgacca cgtccgagct gaggctgaaa ctctcccttc attatcaatt actaagctgg   1020
atctccagtg ggtccaggtt ttgagcgaag gctgggccac tcccctcaaa ggtttcatgc   1080
gggagaagga gtacttacag gttatgcact ttgacacccc tgctagatga tggcgtgatca  1140 acatgagcat ccccattgta ctgcccgtct ctgcagagga taagacacgg ctggaagggt   1200
gcagcaagtt tgtcctggca catggtggac ggagggtagc tatcttacga gacgctgaat   1260
tctatgaaca cagaaaagag gaacgctgtt cccgtgtttg ggggacaaca tgtacaaaac   1320 accccccatat caaaatggtg atggaaagtg gggactggct ggttggtgga gaccttcagg  1380
tgctggagaa aataagatgg aatgatgggc tggaccaata ccgtctgaca cctctggagc   1440
tcaaacagaa atgtaaagaa atgaatgctg atgcggtgtt tgcattccag ttgcgcaatc   1500
ctgtccacaa tggccatgcc ctgttgatgc aggacactcg ccgcaggctc ctagagaggg   1560
gctacaagca cccggtcctc ctactacacc ctctgggcgg ctggaccaag gatgacgatg   1620
tgcctctaga ctggcggatg aagcagcacg cggctgtgct cgaggaaggg gtcctggatc   1680
ccaagtcaac cattgttgcc atcttttccgt ctcccatgtt atatgctggc cccacagagg  1740
tccagtggca ctgcaggtcc cggatgattg cgggtgccaa tttctacatt gtggggaggg   1800
accctgcagg aatgccccat cctgaaaacca agaaggatct gtatgaaccc actcatgggg  1860
gcaaggtctt gagcatggcc cctggcctca cctctgtgga aatcattcca ttccgagtgg   1920
ctgcctacaa caaagccaaa aaagccatgg acttctatga tccagcaagg cacaatgagt   1980
ttgacttcat ctcaggaact cgaatgagga agctcgcccg ggaaggagag aatcccccag   2040
atggcttcat ggcccccaaa gcatggaagg tcctgacaga ttattacagg tccctggaga   2100
agaactaagc ctttggctcc agagtttctt tctgaagtgc tctttgatta ccttttctat   2160
ttttatgatt agatgctttg tattaaattg cttctcaatg atgcatttta atcttttata   2220
atgaagtaaa agttgtgtct ataattaaaa aaaaatatat atatatacac acacacatat   2280
acatacaaag tcaaactgaa gaccaaatct tagcaggtaa aagcaatatt cttatacatt   2340
tcataataaa attagctcta tgtattttct actgcacctg agcaggcagg tcccagattt   2400
cttaaggctt tgtttgacca tgtgtctagt tacttgctga aaagtgaata tattttccag   2460
catgtcttga caacctgtac tcttccaatg tcatttatca gttgtaaaat atatcagatt   2520
gtgtcctctt ctgtacaatt gacaaaaaaa aaaatttttt tttctcactc taaagaggt    2580 gtggctcaca tcaagattct tcctgatatt ttacctcatg ctgtacaaag ccttaatgtt   2640
gtaatcatat cttacgtgtt gaagacctga ctggagaaac aaaatgtgca ataacgtgaa   2700
ttttatctta gagatctgtg cagcctattt ctgtcacaaa agttatattg tctaataaga   2760
gaagtcttaa tggcctctgt gaataatgta actccagtta cacggtgact tttaatagca   2820
tacagtgatt tgatgaaagg acgtcaaaca atgtggcgat gtcgtggaaa gttatctttc   2880
ccgctctttg ctgtggtcat tgtgtcttgc agaaaggatg gccctgatgc agcagcagcg   2940
ccagctgtaa taaaaaataa ttcacactat cagactagca aggcactaga actggaaaag   3000
```

| | |
|---|---|
| accacagaaa acaaagaatc caacccttc atcttacagg tgaacaaact gtgatgatgc | 3060 |
| acatgtatgt gttttgtaag ctgtgagcac cgtaacaaaa tgtaaatttg ccattattag | 3120 |
| gaagtgctgg tggcagtgaa gaagcaccca ggccacttga ctcccagtct ggtgccctgt | 3180 |
| ctacaccaga caacacagga gctgggtcag attcccctca gctgcttaac aaagttcctc | 3240 |
| gaacagaaag tgcttacaaa gctgccttct cggatactga aaggtcgagt tttctgaact | 3300 |
| gcactgattt tattgcagtt gaaaaaaaaa aaaagctatt ccaaagattt caagctgttc | 3360 |
| tgagacatct tctgatggct ttacttcctg agaggcaatg ttttacttt atgcataatt | 3420 |
| cattgttgcc aaggaataaa gtgaagaaac agcaccttt aatatatagg tctctctgga | 3480 |
| agagacctaa attagaaaga gaaaactgtg acaatttca tattctcatt cttaaaaaac | 3540 |
| actaatctta actaacaaaa gttcttttga gaataagtta cacacaatgg ccacagcagt | 3600 |
| ttgtctttaa tagtatagtg cctatactca tgtaatcggt tactcactac tgcctttaaa | 3660 |
| aaaaaaaacc agcatattta ttgaaaacat gagacaggat tatagtgcct taaccgatat | 3720 |
| attttgtgac ttaaaaaata catttaaaac tgctcttctg ctctagtacc atgcttagtg | 3780 |
| caaatgatta tttctatgta caactgatgc ttgttcttat tttaataaat ttatcagagt | 3840 |
| gaaaaaaaaa aaaaaaaa | 3859 |

```
<210> SEQ ID NO 2
<211> LENGTH: 3874
<212> TYPE: DNA
<213> ORGANISM: Homo sapiens
<220> FEATURE:
<221> NAME/KEY: mRNA
<222> LOCATION: (1)...(3874)
<223> OTHER INFORMATION: Homo sapiens 3'-phosphoadenosine
      5'-phosphosulfate synthase 2 (PAPSS2), transcript variant 2, mRNA,
      NM_001015880

<400> SEQUENCE: 2
```

| | |
|---|---|
| ctaggcggcg gcggccgggt ccccaaggct gggcgctgct tgcggaaccg acggggcgga | 60 |
| gaggagcgtg gcgggaggag gagtaggaga aggggctgg tcaagggaag tgcgacgtgt | 120 |
| ctgcggagcc ttttatacc tccttcccgg gagtccggca gccgctgctg ctgctgctgc | 180 |
| tgctgctgcc gccgccgccg ccgccgtccc tgcgtccttc ggtctctgct cccgggaccc | 240 |
| gggctccgcc gcagccagcc agcatgtcgg ggatcaagaa gcaaagacg gagaaccagc | 300 |
| agaaatccac caatgtagtc tatcaggccc accatgtgag caggaataag agagggcaag | 360 |
| tggttggaac aaggggtggg ttccgaggat gtaccgtgtg ctaacaggt ctctctggtg | 420 |
| ctggaaaaac aacgataagt tttgccctgg aggagtacct tgtctcccat gccatccctt | 480 |
| gttactccct ggatgggac aatgtccgtc atggccttaa cagaaatctc ggattctctc | 540 |
| ctggggacag agaggaaat atccgccgga ttgctgaggt ggctaagctg tttgctgatg | 600 |
| ctggtctggt ctgcattacc agctttattt ctccattcgc aaaggatcgt gagaatgccc | 660 |
| gcaaaataca tgaatcagca gggctgccat tctttgaaat atttgtagat gcacctctaa | 720 |
| atatttgtga aagcagagac gtaaaaggcc tctataaaag ggccagagct ggggagatta | 780 |
| aaggattac aggtattgat tctgattatg agaaacctga aactcctgag cgtgtgctta | 840 |
| aaaccaattt gtccacagtg agtgactgtg tccaccaggt agtggaactt ctgcaagagc | 900 |
| agaacattgt accctatact ataatcaaag atatccacga actctttgtg ccggaaaaca | 960 |
| aacttgacca cgtccgagct gaggctgaaa ctctcccttc attatcaatt actaagctgg | 1020 |
| atctccagtg ggtccaggtt ttgagcgaag gctgggccac tcccctcaaa ggtttcatgc | 1080 |

```
gggagaagga gtacttacag gttatgcact tgacaccct gctagatggc atgcccttc      1140 ctgatggcgt gatcaacatg agcatcccca ttgtactgcc cgtctctgca gaggataaga    1200
cacggctgga agggtgcagc aagtttgtcc tggcacatgg tggacggagg gtagctatct    1260
tacgagacgc tgaattctat gaacacagaa aagaggaacg ctgttcccgt gtttggggga    1320
caacatgtac aaaacacccc catatcaaaa tggtgatgga agtggggac tggctggttg     1380 gtggagacct tcaggtgctg gagaaaataa gatggaatga tgggctggac caataccgtc    1440
tgacacctct ggagctcaaa cagaaatgta agaaatgaa tgctgatgcg gtgtttgcat     1500
tccagttgcg caatcctgtc cacaatggcc atgccctgtt gatgcaggac actcgccgca    1560
ggctcctaga gaggggctac aagcacccgg tcctcctact acaccctctg gcggctgga    1620 ccaaggatga cgatgtgcct ctagactggc ggatgaagca gcacgcggct gtgctcgagg   1680 aagggtcct ggatcccaag tcaaccattg ttgccatctt tccgtctccc atgttatatg     1740
ctggccccac agaggtccag tggcactgca ggtcccggat gattgcgggt gccaatttct    1800
acattgtggg gagggaccct gcaggaatgc cccatcctga aaccaagaag gatctgtatg    1860
aacccactca tgggggcaag gtcttgagca tggcccctgg cctcacctct gtggaaatca    1920
ttccattccg agtggctgcc tacaacaaag ccaaaaaagc catggacttc tatgatccag    1980
caaggcacaa tgagtttgac ttcatctcag gaactcgaat gaggaagctc gccgggaag    2040 gagagaatcc cccagatggc ttcatggccc ccaaagcatg gaaggtcctg acagattatt    2100
acaggtccct ggagaagaac taagcctttg gctccagagt ttctttctga agtgctcttt    2160
gattaccttt tctattttta tgattagatg ctttgtatta aattgcttct caatgatgca    2220
ttttaatctt ttataatgaa gtaaaagttg tgtctataat taaaaaaaaa tatatatata    2280
tacacacaca catatacata caaagtcaaa ctgaagacca aatcttagca ggtaaaagca    2340
atattcttat acatttcata ataaaattag ctctatgtat tttctactgc acctgagcag    2400
gcaggtccca gatttcttaa ggctttgttt gaccatgtgt ctagttactt gctgaaaagt    2460
gaatatattt tccagcatgt cttgacaacc tgtactcttc caatgtcatt tatcagttgt    2520
aaaatatatc agattgtgtc ctcttctgta caattgacaa aaaaaaaaat ttttttttct    2580
cactctaaaa gaggtgtggc tcacatcaag attcttcctg atattttacc tcatgctgta    2640
caaagcctta atgttgtaat catatcttac gtgttgaaga cctgactgga gaaacaaaat    2700
gtgcaataac gtgaatttta tcttagagat ctgtgcagcc tatttctgtc acaaagtta    2760 tattgtctaa taagagaagt cttaatggcc tctgtgaata atgtaactcc agttacacgg    2820
tgactttaaa tagcatacag tgatttgatg aaaggacgtc aaacaatgtg gcgatgtcgt    2880
ggaaagttat ctttcccgct ctttgctgtg gtcattgtgt cttgcagaaa ggatggccct    2940
gatgcagcag cagcgccagc tgtaataaaa aataattcac actatcagac tagcaaggca    3000
ctagaactgg aaaagaccac agaaacaaa gaatccaacc ctttcatctt acaggtgaac     3060
aaactgtgat gatgcacatg tatgtgtttt gtaagctgtg agcaccgtaa caaaatgtaa    3120
atttgccatt attaggaagt gctggtggca gtgaagaagc acccaggcca cttgactccc    3180
agtctggtgc cctgtctaca ccagacaaca caggagctgg gtcagattcc cctcagctgc    3240
ttaacaaagt tcctcgaaca gaaagtgctt acaaagctgc cttctcggat actgaaaggt    3300
cgagttttct gaactgcact gatttttattg cagttgaaaa aaaaaaaaag ctattccaaa   3360
gatttcaagc tgttctgaga catcttctga tggctttact tcctgagagg caatgttttt    3420
```

| | | |
|---|---|---|
| actttatgca taattcattg ttgccaagga ataaagtgaa gaaacagcac cttttaatat | 3480 | |
| ataggtctct ctggaagaga cctaaattag aaagagaaaa ctgtgacaat tttcatattc | 3540 | |
| tcattcttaa aaaacactaa tcttaactaa caaaagttct tttgagaata agttacacac | 3600 | |
| aatggccaca gcagtttgtc tttaatagta tagtgcctat actcatgtaa tcggttactc | 3660 | |
| actactgcct ttaaaaaaaa aaaccagcat atttattgaa acatgagac aggattatag | 3720 | |
| tgccttaacc gatatatttt gtgacttaaa aaatacatt t aaaactgctc ttctgctcta | 3780 | |
| gtaccatgct tagtgcaaat gattatttct atgtacaact gatgcttgtt cttattttaa | 3840 | |
| taaatttatc agagtgaaaa aaaaaaaaaa aaaa | 3874 | |

<210> SEQ ID NO 3
<211> LENGTH: 614
<212> TYPE: PRT
<213> ORGANISM: Homo sapiens
<220> FEATURE:
<223> OTHER INFORMATION: Homo sapiens bifunctional 3'-phosphoadenosine
      5'-phosphosulfate synthase 2 isoform a protein

<400> SEQUENCE: 3

Met Ser Gly Ile Lys Lys Gln Lys Thr Glu Asn Gln Gln Lys Ser Thr
 1               5                  10                  15

Asn Val Val Tyr Gln Ala His His Val Ser Arg Asn Lys Arg Gly Gln
            20                  25                  30

Val Val Gly Thr Arg Gly Gly Phe Arg Gly Cys Thr Val Trp Leu Thr
        35                  40                  45

Gly Leu Ser Gly Ala Gly Lys Thr Thr Ile Ser Phe Ala Leu Glu Glu
    50                  55                  60

Tyr Leu Val Ser His Ala Ile Pro Cys Tyr Ser Leu Asp Gly Asp Asn
65                  70                  75                  80

Val Arg His Gly Leu Asn Arg Asn Leu Gly Phe Ser Pro Gly Asp Arg
                85                  90                  95

Glu Glu Asn Ile Arg Arg Ile Ala Glu Val Ala Lys Leu Phe Ala Asp
            100                 105                 110

Ala Gly Leu Val Cys Ile Thr Ser Phe Ile Ser Pro Phe Ala Lys Asp
        115                 120                 125

Arg Glu Asn Ala Arg Lys Ile His Glu Ser Ala Gly Leu Pro Phe Phe
    130                 135                 140

Glu Ile Phe Val Asp Ala Pro Leu Asn Ile Cys Glu Ser Arg Asp Val
145                 150                 155                 160

Lys Gly Leu Tyr Lys Arg Ala Arg Ala Gly Glu Ile Lys Gly Phe Thr
                165                 170                 175

Gly Ile Asp Ser Asp Tyr Glu Lys Pro Glu Thr Pro Glu Arg Val Leu
            180                 185                 190

Lys Thr Asn Leu Ser Thr Val Ser Asp Cys Val His Gln Val Val Glu
        195                 200                 205

Leu Leu Gln Glu Gln Asn Ile Val Pro Tyr Thr Ile Ile Lys Asp Ile
    210                 215                 220

His Glu Leu Phe Val Pro Glu Asn Lys Leu Asp His Val Arg Ala Glu
225                 230                 235                 240

Ala Glu Thr Leu Pro Ser Leu Ser Ile Thr Lys Leu Asp Leu Gln Trp
                245                 250                 255

Val Gln Val Leu Ser Glu Gly Trp Ala Thr Pro Leu Lys Gly Phe Met
            260                 265                 270

Arg Glu Lys Glu Tyr Leu Gln Val Met His Phe Asp Thr Leu Leu Asp

```
            275                 280                 285
Asp Gly Val Ile Asn Met Ser Ile Pro Ile Val Leu Pro Val Ser Ala
    290                 295                 300
Glu Asp Lys Thr Arg Leu Glu Gly Cys Ser Lys Phe Val Leu Ala His
305                 310                 315                 320
Gly Gly Arg Arg Val Ala Ile Leu Arg Asp Ala Glu Phe Tyr Glu His
                325                 330                 335
Arg Lys Glu Glu Arg Cys Ser Arg Val Trp Gly Thr Thr Cys Thr Lys
            340                 345                 350
His Pro His Ile Lys Met Val Met Glu Ser Gly Asp Trp Leu Val Gly
                355                 360                 365
Gly Asp Leu Gln Val Leu Glu Lys Ile Arg Trp Asn Asp Gly Leu Asp
    370                 375                 380
Gln Tyr Arg Leu Thr Pro Leu Glu Leu Lys Gln Lys Cys Lys Glu Met
385                 390                 395                 400
Asn Ala Asp Ala Val Phe Ala Phe Gln Leu Arg Asn Pro Val His Asn
                405                 410                 415
Gly His Ala Leu Leu Met Gln Asp Thr Arg Arg Arg Leu Leu Glu Arg
            420                 425                 430
Gly Tyr Lys His Pro Val Leu Leu Leu His Pro Leu Gly Gly Trp Thr
                435                 440                 445
Lys Asp Asp Asp Val Pro Leu Asp Trp Arg Met Lys Gln His Ala Ala
    450                 455                 460
Val Leu Glu Glu Gly Val Leu Asp Pro Lys Ser Thr Ile Val Ala Ile
465                 470                 475                 480
Phe Pro Ser Pro Met Leu Tyr Ala Gly Pro Thr Glu Val Gln Trp His
                485                 490                 495
Cys Arg Ser Arg Met Ile Ala Gly Ala Asn Phe Tyr Ile Val Gly Arg
            500                 505                 510
Asp Pro Ala Gly Met Pro His Pro Glu Thr Lys Lys Asp Leu Tyr Glu
                515                 520                 525
Pro Thr His Gly Gly Lys Val Leu Ser Met Ala Pro Gly Leu Thr Ser
    530                 535                 540
Val Glu Ile Ile Pro Phe Arg Val Ala Ala Tyr Asn Lys Ala Lys Lys
545                 550                 555                 560
Ala Met Asp Phe Tyr Asp Pro Ala Arg His Asn Glu Phe Asp Phe Ile
                565                 570                 575
Ser Gly Thr Arg Met Arg Lys Leu Ala Arg Glu Gly Glu Asn Pro Pro
            580                 585                 590
Asp Gly Phe Met Ala Pro Lys Ala Trp Lys Val Leu Thr Asp Tyr Tyr
                595                 600                 605
Arg Ser Leu Glu Lys Asn
    610

<210> SEQ ID NO 4
<211> LENGTH: 619
<212> TYPE: PRT
<213> ORGANISM: Homo sapiens
<220> FEATURE:
<223> OTHER INFORMATION: Homo sapiens bifunctional 3'-phosphoadenosine
      5'-phosphosulfate synthase 2 isoform b protein

<400> SEQUENCE: 4

Met Ser Gly Ile Lys Lys Gln Lys Thr Glu Asn Gln Gln Lys Ser Thr
1               5                   10                  15
```

-continued

```
Asn Val Val Tyr Gln Ala His His Val Ser Arg Asn Lys Arg Gly Gln
            20                  25                  30

Val Val Gly Thr Arg Gly Gly Phe Arg Gly Cys Thr Val Trp Leu Thr
        35                  40                  45

Gly Leu Ser Gly Ala Gly Lys Thr Thr Ile Ser Phe Ala Leu Glu Glu
    50                  55                  60

Tyr Leu Val Ser His Ala Ile Pro Cys Tyr Ser Leu Asp Gly Asp Asn
65                  70                  75                  80

Val Arg His Gly Leu Asn Arg Asn Leu Gly Phe Ser Pro Gly Asp Arg
                85                  90                  95

Glu Glu Asn Ile Arg Arg Ile Ala Glu Val Ala Lys Leu Phe Ala Asp
            100                 105                 110

Ala Gly Leu Val Cys Ile Thr Ser Phe Ile Ser Pro Phe Ala Lys Asp
        115                 120                 125

Arg Glu Asn Ala Arg Lys Ile His Glu Ser Ala Gly Leu Pro Phe Phe
    130                 135                 140

Glu Ile Phe Val Asp Ala Pro Leu Asn Ile Cys Glu Ser Arg Asp Val
145                 150                 155                 160

Lys Gly Leu Tyr Lys Arg Ala Arg Ala Gly Glu Ile Lys Gly Phe Thr
                165                 170                 175

Gly Ile Asp Ser Asp Tyr Glu Lys Pro Glu Thr Pro Glu Arg Val Leu
            180                 185                 190

Lys Thr Asn Leu Ser Thr Val Ser Asp Cys Val His Gln Val Val Glu
        195                 200                 205

Leu Leu Gln Glu Gln Asn Ile Val Pro Tyr Thr Ile Ile Lys Asp Ile
    210                 215                 220

His Glu Leu Phe Val Pro Glu Asn Lys Leu Asp His Val Arg Ala Glu
225                 230                 235                 240

Ala Glu Thr Leu Pro Ser Leu Ser Ile Thr Lys Leu Asp Leu Gln Trp
                245                 250                 255

Val Gln Val Leu Ser Glu Gly Trp Ala Thr Pro Leu Lys Gly Phe Met
            260                 265                 270

Arg Glu Lys Glu Tyr Leu Gln Val Met His Phe Asp Thr Leu Leu Asp
        275                 280                 285

Gly Met Ala Leu Pro Asp Gly Val Ile Asn Met Ser Ile Pro Ile Val
    290                 295                 300

Leu Pro Val Ser Ala Glu Asp Lys Thr Arg Leu Glu Gly Cys Ser Lys
305                 310                 315                 320

Phe Val Leu Ala His Gly Gly Arg Arg Val Ala Ile Leu Arg Asp Ala
                325                 330                 335

Glu Phe Tyr Glu His Arg Lys Glu Arg Cys Ser Arg Val Trp Gly
            340                 345                 350

Thr Thr Cys Thr Lys His Pro His Ile Lys Met Val Met Glu Ser Gly
        355                 360                 365

Asp Trp Leu Val Gly Gly Asp Leu Gln Val Leu Glu Lys Ile Arg Trp
    370                 375                 380

Asn Asp Gly Leu Asp Gln Tyr Arg Leu Thr Pro Leu Glu Leu Lys Gln
385                 390                 395                 400

Lys Cys Lys Glu Met Asn Ala Asp Ala Val Phe Ala Phe Gln Leu Arg
                405                 410                 415

Asn Pro Val His Asn Gly His Ala Leu Leu Met Gln Asp Thr Arg Arg
            420                 425                 430

Arg Leu Leu Glu Arg Gly Tyr Lys His Pro Val Leu Leu Leu His Pro
```

```
                435                 440                 445

Leu Gly Gly Trp Thr Lys Asp Asp Val Pro Leu Asp Trp Arg Met
450                 455                 460

Lys Gln His Ala Ala Val Leu Glu Glu Gly Val Leu Asp Pro Lys Ser
465                 470                 475                 480

Thr Ile Val Ala Ile Phe Pro Ser Pro Met Leu Tyr Ala Gly Pro Thr
                485                 490                 495

Glu Val Gln Trp His Cys Arg Ser Arg Met Ile Ala Gly Ala Asn Phe
                500                 505                 510

Tyr Ile Val Gly Arg Asp Pro Ala Gly Met Pro His Pro Glu Thr Lys
                515                 520                 525

Lys Asp Leu Tyr Glu Pro Thr His Gly Gly Lys Val Leu Ser Met Ala
530                 535                 540

Pro Gly Leu Thr Ser Val Glu Ile Ile Pro Phe Arg Val Ala Ala Tyr
545                 550                 555                 560

Asn Lys Ala Lys Lys Ala Met Asp Phe Tyr Asp Pro Ala Arg His Asn
                565                 570                 575

Glu Phe Asp Phe Ile Ser Gly Thr Arg Met Arg Lys Leu Ala Arg Glu
                580                 585                 590

Gly Glu Asn Pro Pro Asp Gly Phe Met Ala Pro Lys Ala Trp Lys Val
                595                 600                 605

Leu Thr Asp Tyr Tyr Arg Ser Leu Glu Lys Asn
610                 615

<210> SEQ ID NO 5
<211> LENGTH: 19
<212> TYPE: RNA
<213> ORGANISM: Artificial Sequence
<220> FEATURE:
<223> OTHER INFORMATION: sense sequence of siRNA for Homo sapiens
      3'-phosphoadenosine 5'-phosphosulfate synthase 2
      (PAPSS2)

<400> SEQUENCE: 5
acaaccugua cucuuccaa                                                 19

<210> SEQ ID NO 6
<211> LENGTH: 19
<212> TYPE: RNA
<213> ORGANISM: Artificial Sequence
<220> FEATURE:
<223> OTHER INFORMATION: antisense sequence of siRNA for Homo sapiens
      3'-phosphoadenosine 5'-phosphosulfate synthase 2
      (PAPSS2)

<400> SEQUENCE: 6
uuggaagagu acagguugu                                                 19

<210> SEQ ID NO 7
<211> LENGTH: 19
<212> TYPE: RNA
<213> ORGANISM: Artificial Sequence
<220> FEATURE:
<223> OTHER INFORMATION: sense sequence of non-specific siRNA

<400> SEQUENCE: 7
ccuacgccac caauuucgu                                                 19

<210> SEQ ID NO 8
<211> LENGTH: 19
<212> TYPE: RNA
```

```
<213> ORGANISM: Artificial Sequence
<220> FEATURE:
<223> OTHER INFORMATION: antisense sequence of non-specific siRNA

<400> SEQUENCE: 8
acgaaauugg uggcguagg                                                   19

<210> SEQ ID NO 9
<211> LENGTH: 20
<212> TYPE: DNA
<213> ORGANISM: Artificial Sequence
<220> FEATURE:
<223> OTHER INFORMATION: forward primer sequence for Homo sapiens
      3'-phosphoadenosine 5'-phosphosulfate synthase 2
      (PAPSS2) cDNA

<400> SEQUENCE: 9
gtctctctgg tgctggaaaa                                                  20

<210> SEQ ID NO 10
<211> LENGTH: 20
<212> TYPE: DNA
<213> ORGANISM: Artificial Sequence
<220> FEATURE:
<223> OTHER INFORMATION: reverse primer sequence for Homo sapiens
      3'-phosphoadenosine 5'-phosphosulfate synthase 2
      (PAPSS2) cDNA

<400> SEQUENCE: 10
tgcgaatgga gaaataaagc                                                  20
```